(12) United States Patent
Venugopal et al.

(10) Patent No.: US 8,144,328 B2
(45) Date of Patent: Mar. 27, 2012

(54) METHODS AND APPARATUS FOR NORMALIZING OPTICAL EMISSION SPECTRA

(75) Inventors: Vijayakumar C. Venugopal, Berkely, CA (US); Eric Pape, Newark, CA (US); Jean-Paul Booth, Oakland, CA (US)

(73) Assignee: Lam Research Corporation, Fremont, CA (US)

( * ) Notice: Subject to any disclaimer, the term of this patent is extended or adjusted under 35 U.S.C. 154(b) by 343 days.

(21) Appl. No.: 12/418,492

(22) Filed: Apr. 3, 2009

(65) Prior Publication Data

US 2009/0251700 A1    Oct. 8, 2009

Related U.S. Application Data

(60) Provisional application No. 61/042,011, filed on Apr. 3, 2008.

(51) Int. Cl.
*G01N 21/00* (2006.01)

(52) U.S. Cl. ........ 356/437; 356/442; 356/316; 356/417; 438/714; 438/9; 438/16; 438/8

(58) Field of Classification Search .......... 356/437–442, 356/315, 316, 417, 719; 438/714, 9, 16, 438/8, 7
See application file for complete search history.

(56) References Cited

U.S. PATENT DOCUMENTS

| | | | |
|---|---|---|---|
| 5,742,380 A | 4/1998 | Ronn | |
| 6,677,604 B2 * | 1/2004 | Mitrovic | ........................ 356/316 |
| 7,399,711 B2 * | 7/2008 | Perry et al. | ........................ 438/7 |
| 2007/0089835 A1 | 4/2007 | Koshimizu et al. | |
| 2007/0095789 A1 | 5/2007 | Davis et al. | |

OTHER PUBLICATIONS

"International Search Report", Issued in PCT Application No. PCT/US2009/039514; Mailing Date: Sep. 28, 2009.
"Written Opinion", Issued in PCT Application No. PCT/US2009/039514; Mailing Date: Sep. 28, 2009.
"International Preliminary Report on Patentability", Issued in PCT Application No. PCT/US2009/039514; Mailing Date: Oct. 14, 2010.

* cited by examiner

*Primary Examiner* — Gregory J Toatley
*Assistant Examiner* — Iyabo S Alli
(74) *Attorney, Agent, or Firm* — IP Strategy Group, P.C.

(57) ABSTRACT

An arrangement for in-situ optical interrogation of plasma emission to quantitatively measure normalized optical emission spectra in a plasma chamber is provided. The arrangement includes a flash lamp and a set of quartz windows. The arrangement also includes a plurality of collimated optical assemblies, which is optically coupled to the set of quartz windows. The arrangement further includes a plurality of fiber optic bundles, which comprises at least an illumination fiber optic bundle, a collection fiber optic bundle, and a reference fiber optic bundle. The arrangement more over includes a multi-channel spectrometer, which is configured with at least a signal channel and a reference channel. The signal channel is optically coupled to at least the flash lamp, the set of quartz windows, the set of collimated optical assemblies, the illuminated fiber optic bundle, and the collection fiber optic bundle to measure a first signal.

19 Claims, 5 Drawing Sheets

METHODS AND APPARATUS FOR NORMALIZING OPTICAL EMISSION SPECTRA

PRIORITY CLAIM

This application is related to and claims priority under 35 U.S.C. §119(e) to a commonly assigned provisional patent application entitled "Methods and Apparatus For Normalizing Optical Emission Spectra," by Venugopal et al., Application Ser. No.61/042,011 filed on Apr. 3, 2008, all of which is incorporated herein by reference.

BACKGROUND OF THE INVENTION

Advances in plasma processing have facilitated growth in the semiconductor industry. During plasma processing, diagnostic tools may be employed to ensure high yield of devices being processed. Optical emission spectroscopy (OES) is often utilized as a diagnostic tool for gas-phase monitoring of etchants and etched products to maintain tight control of process parameters.

In the optical interrogation of plasma, there is a characteristic glow, i.e., specific optical emission spectrum, associated with a plasma discharge. Plasma discharge may have a spectral definition that may be a function of multiple variables including, but not limited to, constituent species, pressure, energy density, driving power, and the like. The spectrum, containing but not limited to deep ultra-violet (UV) through far infra-red (IR) wavelengths, may typically be observed employing a single channel spectrometer.

Optical interrogation of plasma may be performed by collecting the optical emission spectrum via a collimator through a quartz window of a plasma etch chamber. The spectral information, transmitted via a collector fiber optic bundle, may be measured by the signal channel of a spectrometer. With the spectral information from the optical interrogation, a considerable amount of information on constituent species may be collected and analyzed to provide guidance for process monitoring and control during plasma processing. However, optical interrogation of plasma employing OES has mainly been limited to qualitative analysis.

Variability, in particular, may be the main limitation hindering OES from being employed for quantitative analyses in the optical interrogation of plasma in a manufacturing environment. For example, variability may be observed from system-to-system in a device fabrication environment. System-to-system variability may manifest in differences in the conditions between each plasma processing system. In another example, system-to-system variability may be observed between measurement systems, i.e., spectrometer to spectrometer. In yet another example, system-to-system variability may be discerned in the differences in the setup of each distinct plasma processing system with each distinct spectrometer. As can be appreciated by those skilled in the art, variability from system-to-system in optical interrogation of plasma during processing in a manufacturing environment may provide a high level of uncertainty limiting OES from being employed as a quantitative tool for plasma monitoring and/or control.

Another source of variability that may limit OES from being employed for quantitative analyses in a manufacturing environment may be variation within a system. For example, the efficiency of coupling the fiber-optic bundle to the plasma chamber and/or to the spectrometer may be a source of variability within the system.

In another example, the geometry and mechanics of the plasma chamber may lead to variability, e.g., in-situ measurement of plasma signals, within the system. Plasma processing typically employs a low pressure relative to the atmosphere requiring a vacuum chamber. A window in the vacuum-chamber wall may need to be of a suitable material, e.g., the window may be constructed from quartz, to transmit in the desired wavelength dependent attenuation along the optical path to measure the plasma spectral signal. However, pressure control in some plasma processing system may employ a confinement ring setup which may partially occlude the optical path between the plasma and the spectrometer. Furthermore, the confinement rings may move relative to the interrogation window(s) depending on the desired plasma pressure and may also experience deposition and/or etching. Thus, the occlusion of the optical path, the deposition, and/or the etching may induce variability within the system making quantitative analysis employing OES impractical.

Variability due to degradation of components as a function of time, i.e., time-to-time variation, may be yet another source of variation impeding OES from being employed for quantitative analysis of plasma processes. For example, the aforementioned quartz window may be exposed to plasma during plasma processing and may experience deposition and/or etching. Thus over time, the quartz window may cloud up and may change the optical property of the window. Typically, clouding of the quartz window may result in lower plasma signal intensity in a nonlinear manner. In another time-to-time variability example, a fiber optic bundle may degrade in optical transmission efficiency as a function of time which may also result in lower plasma signal intensity in a nonlinear manner. As may be appreciated from the foregoing, time-to-time variability may provide yet another source of uncertainty limiting the OES from being employed as a quantitative tool.

In general, many of the variables that define plasma may be difficult to accurately measure in-situ. Also, there may be significant fluctuations at multiple time scales in plasma which may result in changes in spectral emission. Due to the variability associated with current optical interrogation of plasma employing OES, the task of quantitatively determining what plasma variables may cause emission changes may be extremely difficult. Thus, the use of OES may be limited to only qualitative applications such as end-point detection, leak identification, species identification, and the like.

A potential solution may entail employing controls to standardize OES to reduce variability at each step in the process. For example, calibrations may be performed to reduce variation between systems and/or instrument. Quartz windows may periodically be cleaned to reduce clouding. Fiber-optic bundles may be replaced to attain original transmission efficiency. Keyed connectors may be employed to mount optical couplers the same way to reduce set-up variability.

However, calibrations and controls may be amenable to laboratory environment but may not be conducive to a manufacturing environment. In high volume manufacturing facilities which may fabricate devices with over a hundred manufacturing steps at high throughput, calibrations and controls after each step may be impractical. The calibrations of uncontrolled variations and time related degradations may require specialized resources. Specialized resources may add cost to a manufacturing process that are extremely cost competitive. Careful calibrations and controls may add time overhead to processing time increasing the cost per device being manufactured and decreasing throughput. Thus, the controls may reduce variability without addressing the capability for quantitative OES measurements while penalizing the process with higher cost and lower throughput.

In view of the foregoing, there are desired methods and apparatus for employing OES as a quantitative tool for process monitoring and control during plasma processing.

BRIEF SUMMARY OF THE INVENTION

The invention relates, in an embodiment, to an arrangement for in-situ optical interrogation of plasma emission to quantitatively measure normalized optical emission spectra in a plasma chamber. The arrangement includes a flash lamp and a set of quartz windows. The arrangement also includes a plurality of collimated optical assemblies, which is optically coupled to the set of quartz windows. The arrangement further includes a plurality of fiber optic bundles, which comprises at least an illumination fiber optic bundle, a collection fiber optic bundle, and a reference fiber optic bundle. The arrangement more over includes a multi-channel spectrometer, which is configured with at least a signal channel and a reference channel. The signal channel is optically coupled to at least the flash lamp, the set of quartz windows, the set of collimated optical assemblies, the illuminated fiber optic bundle, and the collection fiber optic bundle to measure a first signal.

The above summary relates to only one of the many embodiments of the invention disclosed herein and is not intended to limit the scope of the invention, which is set forth in the claims herein. These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF EMBODIMENTS

The present invention will now be described in detail with reference to a few embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In accordance with embodiments of the invention, there are provided methods and arrangements for in-situ optical interrogation of plasma emission to quantitatively measure normalized optical emission spectra across multiple chambers. In an example, the in-situ measurements of optical collection efficiency may be performed by interrogating the optical collection path in real time employing an external light source through diametrically opposite view ports in an embodiment.

In an embodiment, the normalized OES measurement system may be configured with an external light source, e.g., Xenon flash lamp. In an example, the flash lamp may have a relatively short pulse width and/or high intensity signal. In an embodiment, a multi-channel spectrometer may be employed to simultaneously measure the emitted signals from a plasma processing chamber and/or the flash lamp output per pulse. Thus, the normalized OES system may allow for the measurements of optical emission and/or optical collection efficiency to attain normalized optical emission spectra. In contrast, prior art OES measurement system may not be configured with an external light source and/or a multi-channel spectrometer.

In an embodiment, fixed coupling factors may be determined by employing off-line calibration measurements. In an example, a calibration may be performed employing a calibrated light source in an embodiment. In another embodiment, a calibration may be performed employing a standard light source that may be measured by both the signal channel and/or the reference channel of the multi-channel spectrometer. These calibrations may be performed once at the spectrometer manufacturer, before shipping the OES system, to determine the fixed coupling factors. Thus, the device manufacturer is not burdened with calibrations that may add cost to the device fabrication process.

In the prior art, method for optical interrogation of plasma employing OES has been limited to qualitative analysis. In the disclosure herein, a method for normalized OES measurements in real time employing a single channel of the spectrometer is discussed, in an embodiment. The normalized OES measurement may account for the drift due to aging in the system and the changes in the optical path due to confinement ring position. In another embodiment, a method for normalized OES measurements in real time employing a multi-channel spectrometer with external calibration measurements is discussed. The spectrometer and optical efficiency factors may be calibrated off-line with the aforementioned calibration methods. In an embodiment, the optical emission spectra may be measured and normalized to remove the variations associated with the optical collection efficiency of the measurement system. As may be appreciated from the foregoing, the aforementioned methods may facilitate quantitative analyses of normalized OES spectrum in real time across different processing chambers.

The features and advantages of the present invention may be better understood with reference to the figures and discussions (with prior art mechanisms and embodiments of the invention contrasted) that follow.

Figure 1:
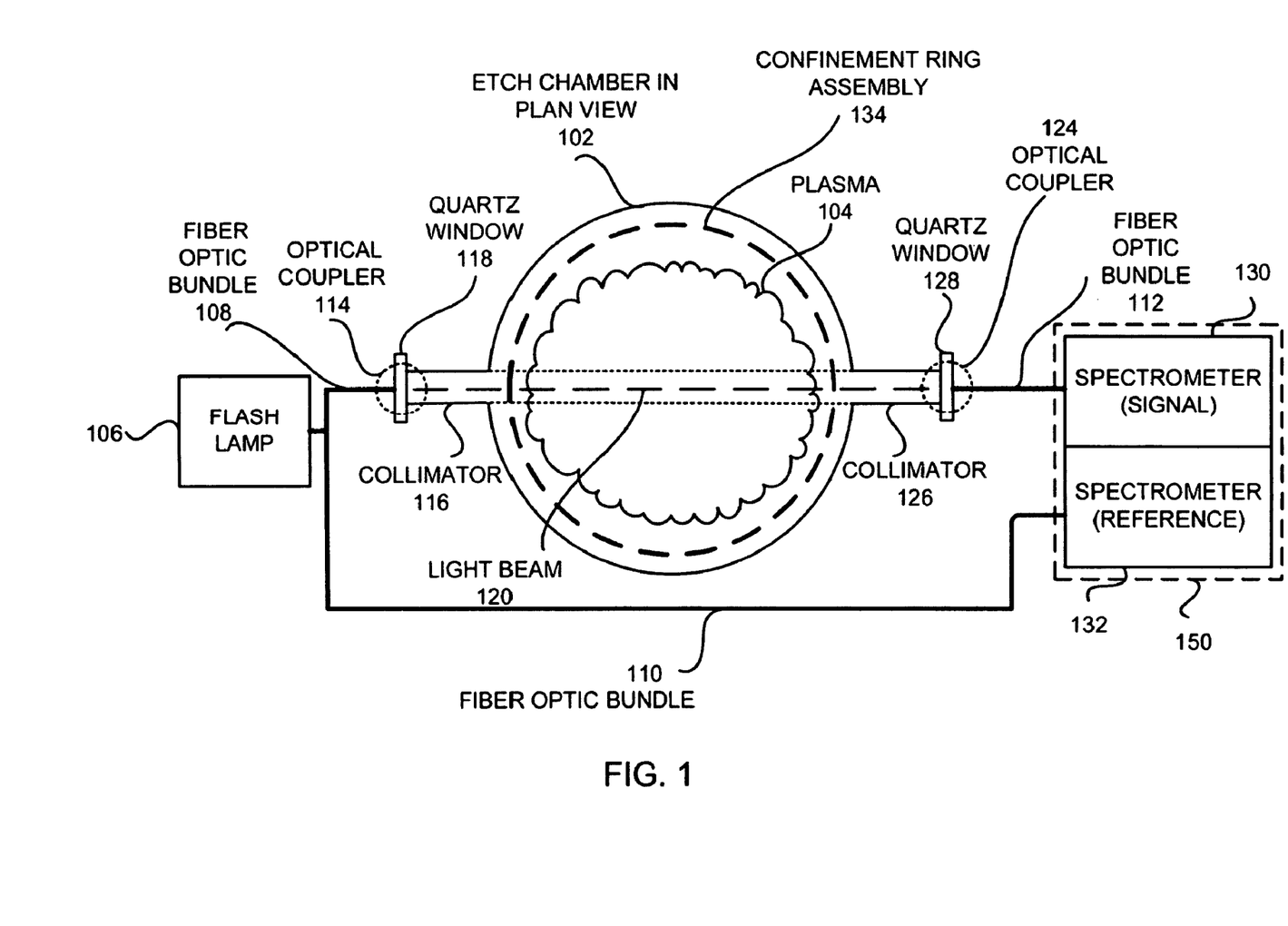
FIG. 1 shows, in accordance with an embodiment of the invention, a simplified schematic of a normalized Optical Emission Spectroscopy (OES) setup in a typical plasma processing system for optical interrogation of plasma.

FIG. 1 shows, in accordance with an embodiment of the invention, a simplified schematic of a normalized Optical Emission Spectroscopy (OES) setup in a typical plasma processing system for optical interrogation of plasma.

In the implementation of FIG. 1, the optical interrogation of plasma 104 in an etch chamber 102 may be performed to measure optical emission spectra that may be independent of the optical efficiencies associated with variations in the measurement system. In an embodiment, etch chamber 102 may be configured with an optional confinement ring assembly 134. Furthermore, etch chamber 102 may be configured with two diametrically opposing quartz windows through which plasma 104 may be visible, in an embodiment. In an example, etch chamber 102 may be configured with a first quartz window 118 on an illumination side and a second quartz window 128 on a collection side.

As the term is employed herein, the illumination side may be the side of the etch chamber that may be configured with an external light source to deliver light source through first quartz window 118. Whereas, the collection side may be the side of the etch chamber that optical emission spectra associated with plasma discharged may be measured by a spectrometer through second quartz window 128.

In an embodiment, a plurality of collimated optical assemblies, e.g., a first collimator 116 and a second collimator 126, may be employed to couple the two quartz windows to etch chamber 102. In an example, quartz window 118 may be coupled to the illumination side of etch chamber 102 with first collimator 116. Similarly, quartz window 128 may be coupled to the collection side of etch chamber 102 with second collimator 126.

In an embodiment, the collimated optical assemblies, coupled at each quartz windows, may be configured with converging and/or diverging optics (not shown to simplify illustration) that may have pre-determined angular acceptance for fiber optic coupling.

For example on the illumination side, the light signal from an external light source, i.e., a flash lamp 106, may be delivered into etch chamber 102 via a first fiber optic bundle 108, in an embodiment. Fiber optic bundle 108 may also be referred to as an illumination fiber optic bundle 108, herein. The flash lamp 106 may be, but not limited to, a Xenon flash lamp capable of delivering a high-intensity, short-pulse light beam 120. The illumination fiber optic bundle 108 may be configured to couple at a first end to flash lamp 106 and to couple at a second end to quartz window 118 via an optical coupler 114, in an embodiment.

In the implementation of FIG. 1, the light signal 120 being delivered via illumination fiber optic bundle 108 into etch chamber 102 may be collimated through collimator 116. In an embodiment, the intensity of light signal 120 may be several orders of magnitude higher in intensity relative to plasma 104, resulting in high signal to noise ratio. The light signal 120 and the optical emission spectra of plasma 104 may be collimated through collimator 126 to be transmitted to a signal channel 130 of multi-channel spectrometer 150 via a second fiber optic bundle 112, in an embodiment. Fiber optic bundle 112 may be referred to as a collection fiber optic bundle 112, herein.

On the collection side, collection fiber optic bundle 112 may be configured to couple at a first end to quartz window 128 via an optical coupler 124 and to couple at a second end to the signal channel 130 of multi-channel spectrometer 150, in an embodiment. The optical emission spectra of plasma 104 and/or light signal 120 from etch chamber 102 may be collected and delivered via collection fiber optic bundle 112 to signal channel 130 on multi-channel spectrometer 150 for measurement, in an embodiment. In an embodiment, signal channel 130 may be, but not limited to, a charged-coupled device (CCD). Thus, signal channel 130 may be configured to measure the transmitted signal(s) from etch chamber 102.

In the implementation of FIG. 1, light signal from flash lamp 106 may be directly collected and transmitted via a third fiber optic bundle 110 to be measured on a reference channel 132 on multi-channel spectrometer 150, in an embodiment. Fiber optic bundle 110 may be referred to as a reference fiber optic bundle 110, herein. Thus, reference channel 132 may be configured to measure the output per pulse of flash lamp 106.

As may be appreciated from the foregoing, the normalized OES setup of FIG. 1, in contrast to prior art, may be configured with an external flash lamp and a multi-channel spectrometer to facilitate method(s), as detailed below, to collect and measure in-situ optical emission spectra that may be independent of optical collection efficiencies associated with the measurement system. By employing the multi-channel spectrometer, measurements of transmitted light from etch chamber and/or flash lamp output per pulse may be made simultaneously to enable normalization of optical emission spectra.

As aforementioned, the measurement system may contain a plurality of optical collection efficiencies that may contribute to variability in OES measurements. The optical collection efficiencies may be decoupled and quantified for normalized OES measurements. Referring to FIG. 1, the optical coupling factors of interest in the normalized OES setup are as follows:

$C_{LR}$: coupling of flash lamp 106 output into reference channel fiber optic bundle 110, $C_{LS}$: coupling of flash lamp 106 output into signal channel fiber optic bundle 108, $C^*_{FL}$: fiber optic transmittance of illumination segment 108 (*—changes over time), $C^*_{FR}$: fiber optic transmittance of reference segment 110 (*—changes over time), $C^*_{FC}$: fiber optic transmittance of collection segment 112 (*—changes over time), $C_R$: coupling efficiency and detector sensitivity of reference channel 132 of multi-channel spectrometer, $C_S$: coupling efficiency and detector sensitivity of signal channel 130 of multi-channel spectrometer, $C^{}_C$: coupling efficiency of collimator assembly 126, quartz window 128 transmittance, and confinement ring 134 transmittance at collection viewport (—changes a lot over time and during a process), and $C^{}_L$: coupling efficiency of collimator assembly 116, quartz window 118 transmittance, and confinement ring 134 transmittance at illumination viewport (—changes a lot over time and during a process).

Figure 2:
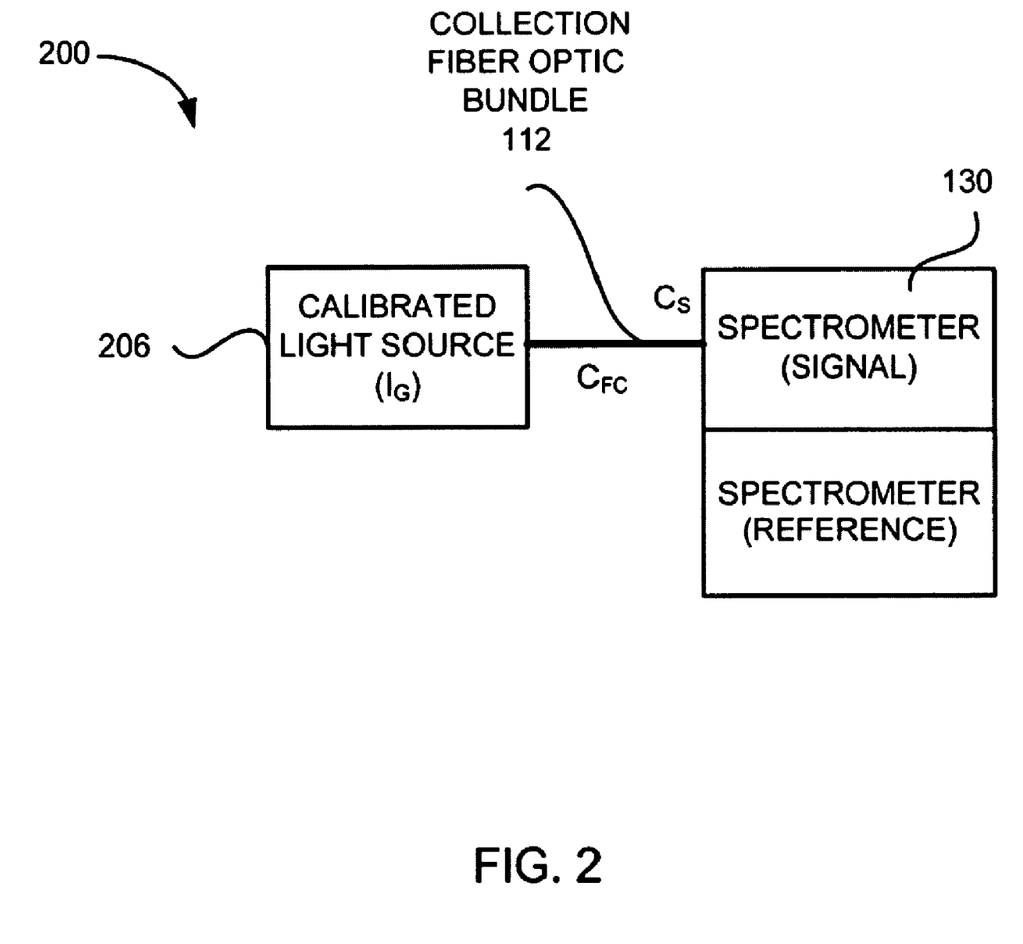
FIG. 2 shows, in accordance with an embodiment of the invention, a simplified schematic of a first calibration setup employing a calibrated light source.

In an embodiment, the fixed coupling factors may be determined by employing two off-line calibration measurements. FIG. 2 shows, in accordance with an embodiment of the invention, a simplified schematic of a first calibration setup 200 employing a calibrated light source.

In the implementation of FIG. 2, the calibration may employ a calibrated light source 206 to determine coupling factor(s) $C_S$ and/or $C_{FC}$, in an embodiment. The calibrated light source 206 may be measured by signal channel 130 of multi-channel spectrometer, in an embodiment of the invention. The output of calibrated light source 206, $I_G$, may be measured as spectrum $L_{Gs}$ on signal channel 130. Coupling factor(s) $C_S$ and/or $C_{FC}$ may be determined as follows:

$$L_{GS}=C_{FC}C_S I_G \quad \text{(equation 1)},$$

where $L_{GS}$ is the measured spectrum, $I_G$ is the known output of the calibrated light source, $C_S$ is the coupling efficiency and detector sensitivity of the signal channel of multi-channel spectrometer, and $C_{FC}$ is the fiber optic transmittance of collection segment 112.

In the implementation of FIG. 2, the determination of $C_{FC}$ for collection fiber optic bundle 112 may be optional, in an embodiment. If the calibration includes the determination of $C_{FC}$, collection fiber optic bundle 112 may be shipped together with signal channel 130 of the multi-channel spectrometer as a matched pair, in an embodiment.

Referring to FIG. 2, $L_{GS}$ and $I_G$ may be known values. However, $L_{GS}$ and $I_G$ may not necessary be absolute values. In an embodiment, $L_{GS}$ may be relative to a golden spectrometer designated by the manufacturer. $I_G$ may be relative to a standard from National Institute of Standards and Technology (NIST). In an embodiment, the calibration may be performed off-line once at the manufacturer to determine the coupling factors $C_S$ and/or $C_{FC}$, prior to shipping to a customer.

As the term is employed herein, a golden spectrometer may be a specific spectrometer designated by the spectrometer manufacturer as nominally representative of a class of spectrometers that may be manufactured by the manufacturer. Thus, subsequent manufactured spectrometers may be calibrated against the golden spectrometer.

Figure 3:
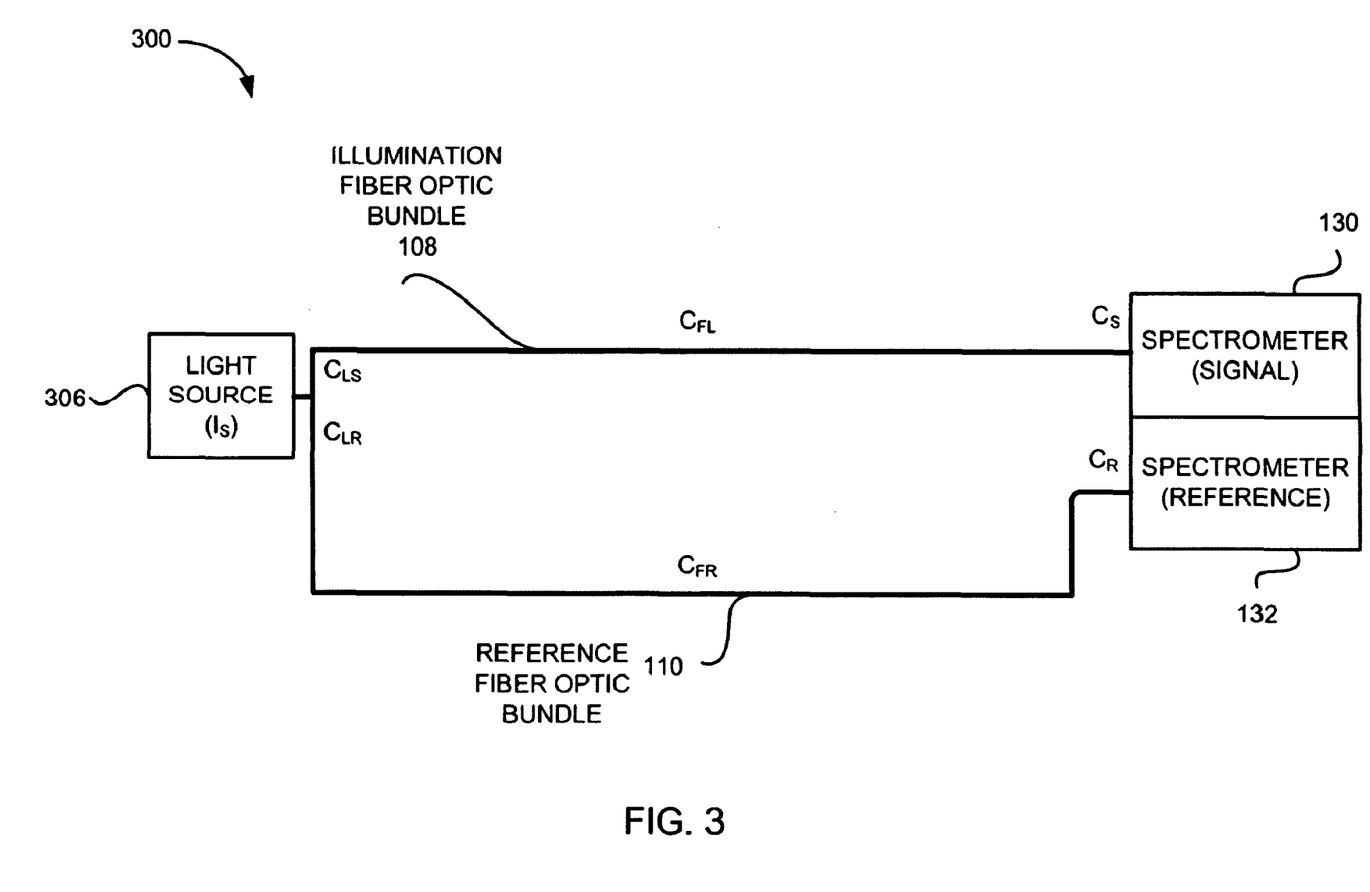
FIG. 3 shows, in accordance with an embodiment of the invention, a simplified schematic of a second calibration setup employing a standard light source.

FIG. 3 shows, in accordance with an embodiment of the invention, a simplified schematic of a second calibration setup 300 employing a standard light source.

In the implementation of FIG. 3, the calibration may employ a standard light source 306 to determine coupling factors $C_R$, $C_S$, $C_{FR}$, $C_{FL}$, $C_{LR}$ and/or $C_{LS}$, in an embodiment. The calibration may employ standard light source 306 that may be measured by both signal channel 130 and reference channel 132 of the multi-channel spectrometer, in an embodiment of the invention. The output of standard light source 306, $I_S$, may be measured as spectrum $L_{GSA}$ on signal channel 130 and spectrum $L_{GRA}$ on reference channel 132. Coupling factors $C_R$, $C_S$, $C_{FR}$, $C_{FL}$, $C_{LR}$ and/or $C_{LS}$ may be determined as follows:

$$L_{GRA} = C_{LR} C_{FR} C_R I_S \quad \text{(equation 2)},$$

$$L_{GSA} = C_{LS} C_{FL} C_S I_S \quad \text{(equation 3)},$$

where $L_{GRA}$ is the measured spectrum on reference channel 132, $L_{GSA}$ is the measured spectrum on signal channel 130, I, is the output of the standard light source, $C_S$ is the coupling efficiency and detector sensitivity of the signal channel of multi-channel spectrometer, $C_R$ is the coupling efficiency and detector sensitivity of the reference channel of multi-channel spectrometer, $C_{LR}$ is the coupling of flash lamp 306 output into reference channel fiber optic bundle 110, $C_{LS}$ is the coupling of flash lamp 306 output into signal channel fiber optic bundle 108, $C_{FL}$ is the fiber optic transmittance of illumination segment 108, and $C_{FR}$ is the fiber optic transmittance of reference segment 110.

In an embodiment, the calibration may be performed off-line once at the manufacturer to determine the coupling factors $C_R$, $C_S$, $C_{FR}$, $C_{FL}$, $C_{LR}$ and/or $C_{LS}$, prior to shipping to a customer.

In the implementation of FIG. 3, the output from standard light source 306, $I_S$, may not have to be a calibrated light source, in an embodiment. The light source 306 may be a flash lamp similar to the flash lamp being employed in the real time OES measurements. In an embodiment, the output cone of light from light source 306 may be configured to overfill fiber bundle inputs.

Referring to FIG. 3, the coupling factor $C_{FR}$ of reference fiber optic bundle 110 may be configured to be substantially equivalent to coupling factor $C_{FL}$ of illumination fiber optic bundle 108, in an embodiment. For example, fiber optic bundle of reference segment 110 may be manufactured to have equivalent length of fiber optic bundle of illumination segment 108, in an embodiment.

To achieve equivalent length, the fiber optic bundles may be manufactured by a plurality of methods. In an example, the fiber optic bundles may be manufactured to a predetermined length with a tight tolerance to attain fiber segment bundles of equivalent length. Alternatively, a pair of fiber optic bundles with equivalent length may be selected in the manufacturing of a plurality of fiber optic bundles. Each pair of fiber optic bundles may need to have equivalent length to each other to serve as a matched pair to be selected for a spectrometer. Thus, the fiber optic bundles pair selected for each OES system may not need to be specified to a tight tolerance that may increase cost in manufacturing.

As may be appreciated from the foregoing, FIG. 2 and FIG. 3 shows two off-line calibration measurements that may be performed once at the manufacturer to determine a plurality of fixed coupling factors before shipping calibrated OES systems to the customers in an embodiment. Since the calibrations of the OES systems are performed once at the spectrometer manufacturer, a device manufacturer is not burdened with tedious calibrations that may add aforementioned overheads to the device manufacturing cost.

Figure 4:
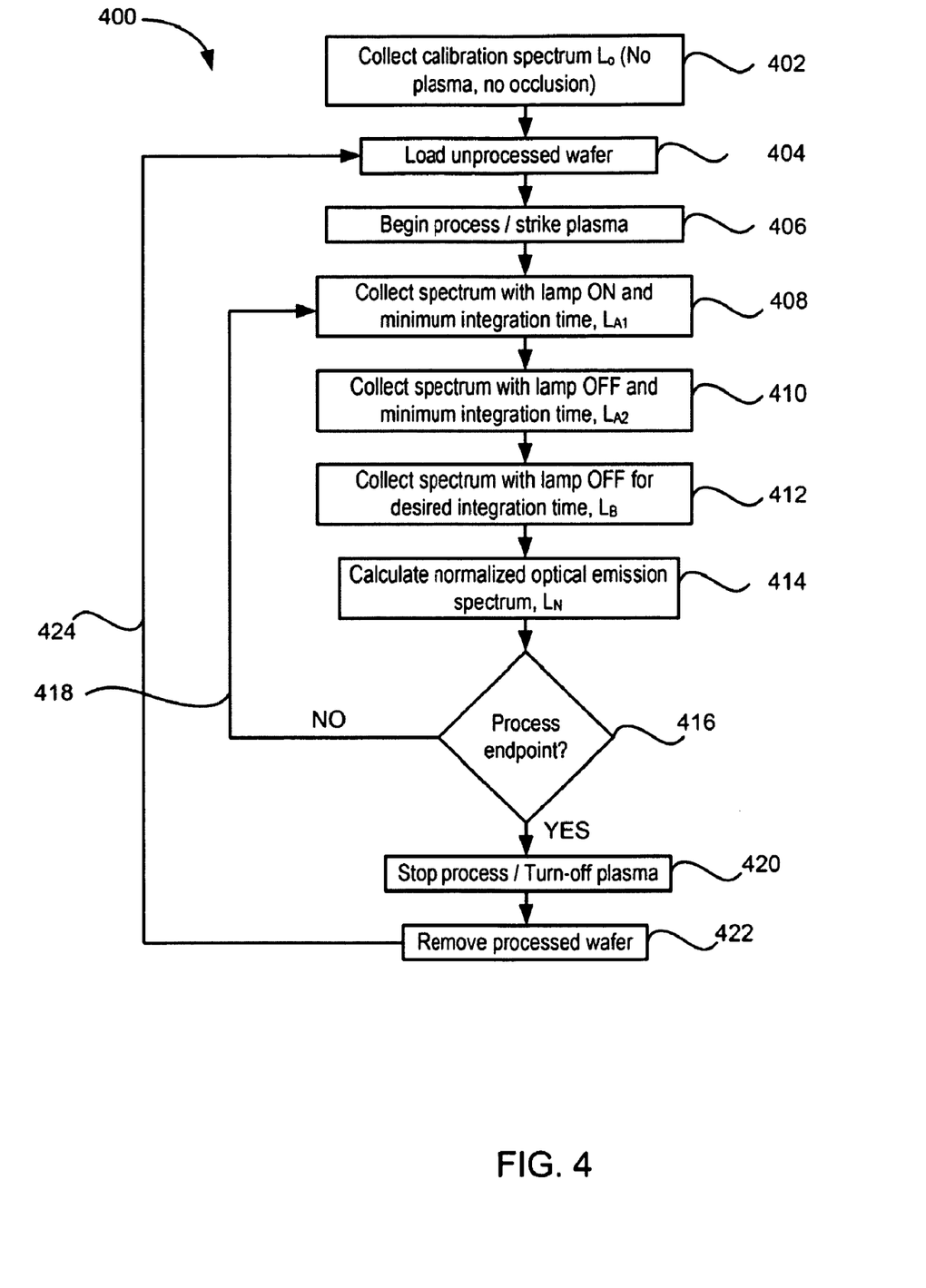
FIG. 4 shows, in accordance with an embodiment of the invention, a simplified flowchart of a method for normalized OES measurements in real time employing a signal channel.

FIG. 4 shows, in accordance with an embodiment of the invention, a simplified flowchart of a method 400 for normalized OES measurements in real time employing a signal channel. FIG. 4 may be discussed in relation to FIG. 1 and FIG. 2 to facilitate understanding.

In an example, the normalized Optical Emission Spectroscopy (OES) setup in a typical plasma processing system of FIG. 1 may be employed for optical interrogation of plasma.

As shown in FIG. 4, a calibration spectrum $L_O$ may be recorded, in step 402, to capture the state of the entire optical system at an initial time in an embodiment. In the initial state, the data from the calibration spectrum $L_O$ may be collected with no plasma and/or no occlusion, e.g., quartz confinement rings.

In step 404, an unprocessed substrate may be loaded into an etch chamber for processing.

In step 406, RF power may be supplied to the etch chamber to react with gases in the chamber to strike plasma, and the processing of the substrate may commence. During plasma processing of the substrate, confinement rings may optionally be employed as require by the process recipe. As may be appreciated from the following, the measured signal may be significantly modulated due to factors such as occlusion by confinement rings in the optical collection path.

In step 408, signals from the etch chamber may be collected with flash lamp "ON" for a minimum integration time to measure spectrum $L_{A1}$ in an embodiment. In an example, the signals from the etch chamber may include the signal from the lamp, the signal from plasma, and various background noises, e.g., dark noise from the spectrometer detector.

In step 410, signals from etch chamber may be collected with flash lamp "OFF" for a minimum integration time to measure spectrum $L_{A2}$ in an embodiment.

As the term is employed herein, the minimum integration time is the minimal time to collect the spectrum. In an embodiment, steps 408 and 410 may be designed to measure the intensity of the flash lamp in real time. In an example, the flash lamp may typically have a relatively short pulse width, approximately in the order of a few microseconds. However, the spectrometer may be limited by electronic circuitry capable of measuring the raw spectrum data in the order of milliseconds due to cost consideration. Although the integration time may only need to be as long as the flash lamp pulse width, the integration time may be longer than the flash lamp pulse width. Thus, the minimum integration time to collect a spectrum may be the result of the cost and/or design limitation of the electronic circuitry.

In an example, real time OES measurement may be made in strobe mode. Spectrum $L_{A1}$ may be measured with the lamp "ON" to measure transmittance of lamp signal, plasma emission and background noises, in an embodiment. In another embodiment, spectrum $L_{A2}$ may be measured with the lamp "OFF" to measure plasma emission and background noises. Thus, the difference of spectrum $L_{A1}$ from spectrum $L_{A2}$, i.e., $(L_{A1}-L_{A2})$, may normalize out plasma emission and background noise to provide the measured spectrum from the lamp in real time.

As may be appreciated by the foregoing, the integration time may be minimized relative to the lamp to measure the light spectrum transmitted through the system and essentially remove the plasma emission and/or background noise. Thus, for a high signal to noise ratio of light transmitted from the lamp to plasma noise, a minimum integration time relative to flash lamp pulse width and/or a high intensity a flash lamp relative to plasma intensity may be desired.

In step 412, signals may be collected from etch chamber with flash lamp "OFF" for the desired integration time to measure spectrum LB in an embodiment. Spectrum $L_B$ may typically be the spectra that may be collected in the prior art that essentially has a plurality of variations associated with the measurement.

In step 414, a normalized optimal emission spectrum $L_N$ may be calculated, in an embodiment, employing equation 4 to normalize out the variations associated with the measurement system, as follows:

$$L_N = L_B / ((L_{A1}-L_{A2})/L_O)^{1/2} \quad \text{(equation 4)},$$

where $(L_{A1}-L_{A2})/L_O$ may be the normalized lamp spectrum in real time relative to the calibrated spectrum without plasma and/or occlusion. Correspondingly, $L_B$ may be normalized to $((L_{A1}-L_{A2})/L_O)^{1/2}$ to give the desired $L_N$ in real time.

In step 416, the process end point may be assessed in an embodiment. The process endpoint may be determined by the emission spectrum from $L_N$ or other methods, such as a preset time or other methods of detecting process endpoint.

If the process has not reached the endpoint, real time OES measurements may be continued to be collected in step 418 by looping back to step 408 in an embodiment. The normalized OES measurements may continue until the process has reached the endpoint. In an embodiment, loop 418 for steps 408 through 416 is the real time OES measurements.

In step 420, the process may be stopped and plasma may be turned off when the process has reached the endpoint in an embodiment.

In step 422, the processed wafer may be removed from the etch chamber in an embodiment.

In step 424, the process may continue and loop back to step 404 where a new wafer may be loaded into the etch chamber. The real time OES measurements may be collected for the processing of another wafer.

As may be appreciated from the foregoing, normalization method 400 may employ only a single channel of the spectrometer without off-line external calibration measurements. Although chamber-to-chamber matching may not be possible, measurement consistency over time is relatively reliable. The measurement may be able to account for the drift due to aging in the system, i.e., deposition on quartz window, and the changes in the optical path due to confinement ring position.

Alternatively and/or additionally, reasonable chamber-to-chamber matching may be accomplished through careful manufacturing control of system components in an embodiment. For example, the matching of spectrometers and fiber bundles, designing of keyed attachment systems, and/or having tight tolerances may give good chamber-to-chamber results without employing external calibration measurements. Thus, a relatively low cost, normalized OES system for diagnostic purpose may be achieved.

Alternatively and/or additionally, a simple off-line calibration, e.g., calibration method of FIG. 2, may be performed once at the spectrometer manufacturer to reduce the approximations that need to be made. By employing OES system with off-line calibration, method 400 may be able to provide matched signals across different etching chambers.

Figure 5:
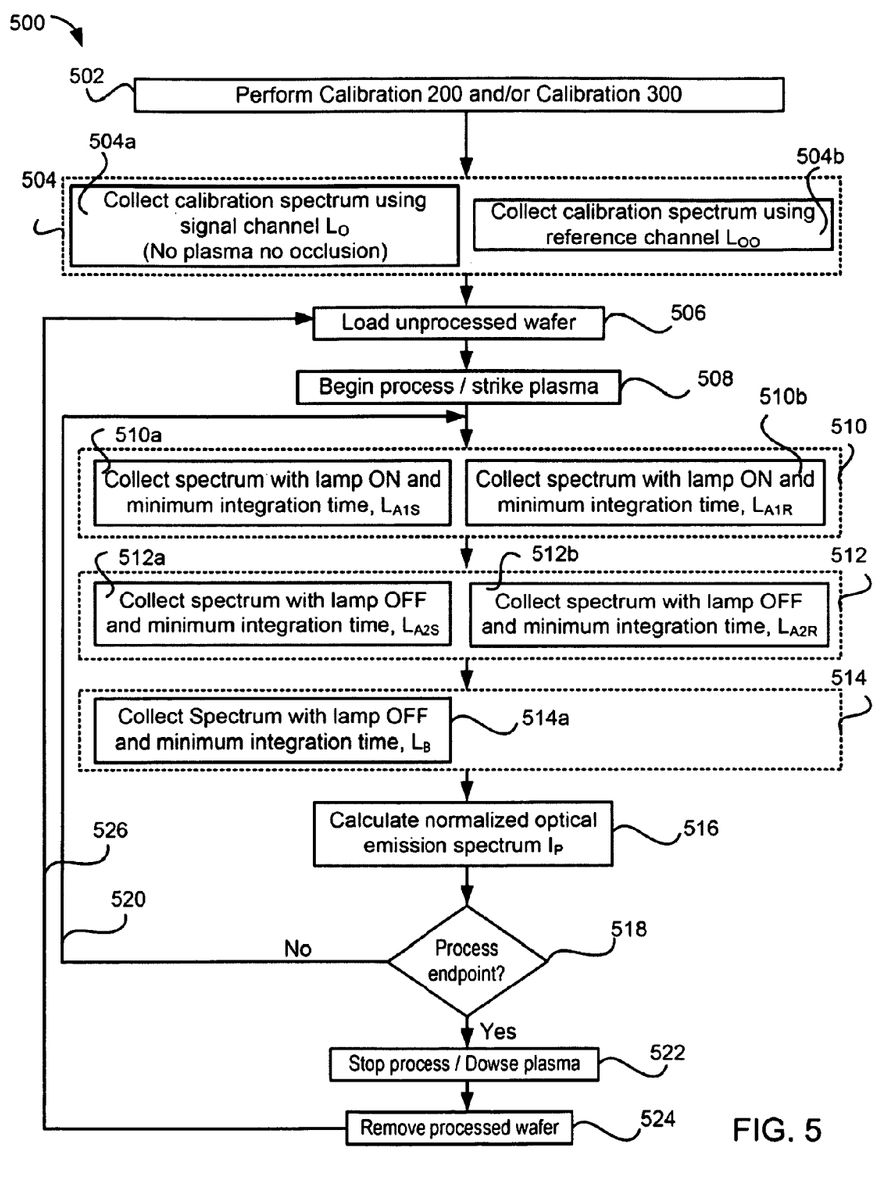
FIG. 5 shows, in accordance with an embodiment of the invention, a simplified flowchart of a method for normalized OES measurements in real time employing a multi-channel spectrometer.

FIG. 5 shows, in accordance with an embodiment of the invention, a simplified flowchart of a method 500 for normalized OES measurements in real time employing a multi-channel spectrometer.

Consider the situation wherein, for example, the normalized Optical Emission Spectroscopy (OES) setup in a typical plasma processing system of FIG. 1 may be employed for optical interrogation of plasma.

In step 502, the spectrometer and optical efficiency factors may be calibrated off-line employing calibration 200 of FIG. 2 and/or calibration 300 of FIG. 3 in an embodiment. Calibration 200 and calibration 300 have been discussed in detail in FIG. 2 and FIG. 3 respectively. The two calibrations may be performed off-line at the manufacturer prior to shipping the system.

In step 504, two calibration steps may be performed. A calibration spectrum Lo may be performed, in step 504a, to capture the state of the entire optical system at an initial time employing the signal channel in an embodiment. In the initial state, the data from the calibration spectrum $L_O$ may be collected with no plasma and/or no occlusion, e.g., quartz confinement rings. In step 504b, the calibration spectrum $L_{OO}$ may be performed employing the reference channel in an embodiment.

Step 504a and/or 504b may not be integral to the real time OES normalization process. However, $L_O$ and/or $L_{OO}$ may be useful to decouple the effect of aging for components such as quartz window and/or collection fiber segment. For example, the effect of aging due to deposit on the quartz window over time may be determined by tracking the $L_O$ and/or $L_{OO}$ as a function of time.

In step 506, an unprocessed substrate may he loaded into an etch chamber for processing.

In step 508, RF power may be supplied to the etch chamber to strike plasma to begin the processing of the substrate. During plasma processing of the substrate, confinement rings may optionally be employed as required by the process recipe.

In step 510, the spectrum from the etch chamber may be collected with the lamp "ON" for a minimum integration time, in step 510a, to measure spectrum $L_{A1S}$ employing the signal channel of the multi-channel spectrometer in an embodiment.

In step 510b, the spectrum $L_{A1R}$ may be collected with the lamp "ON" for a minimum integration time employing the reference channel of the multi-channel spectrometer in an embodiment.

In step 512, the spectrum from the etch chamber may be collected with the lamp "OFF" for a minimum integration time, in step 512a, to measure spectrum $L_{A2S}$ employing the signal channel of the multi-channel spectrometer in an embodiment.

In step 512b, the spectrum $L_{A2R}$ may be collected with the lamp "OFF" for a minimum integration time employing the reference channel of the multi-channel spectrometer in an embodiment.

As aforementioned, the light signal from the flash lamp, e.g., Xenon flash lamp, may be a high-intensity, short-pulse light beam. The intensity of the flash lamp may be several orders of magnitude higher than the plasma emission resulting in high signal to noise ratio. In addition, the pulse width of the flash lamp may be relatively short, e.g., a few microseconds, in comparison to the time scale, i.e. integration time, of the electronic circuitry for capturing the spectrum. The limiting factor in the integration time, e.g., in milliseconds, for capturing the spectrum may be the electronic circuitry.

The spectrum $L_{AS}$ measured on the signal channel may be determined from step 510*a* and step 512*a*, as follows:

$$L_{AS}=L_{A1S}-L_{A2S} \quad \text{(equation 5)},$$

where $L_{AS}$ may be related to the coupling factors, as follows:

$$L_{AS}=C_{LS}C^*_{FL}C^{}_{L}C^{}_{C}C^*_{FC}C_{S}I_{A} \quad \text{(equation 6)},$$

where $I_A$ is the output of the flash lamp.

The spectrum $L_{AR}$ measured on the reference channel may be determined from step 510*b* and step 512*b*, as follows:

$$L_{AR}=L_{A1R}-L_{A2R} \quad \text{(equation 7)},$$

where $L_{AR}$ may be related to the coupling factors, as follows:

$$L_{AR}=C_{LR}C^*_{FR}C_{R}I_{A} \quad \text{(equation 8)}.$$

The calculation from equation 5 and equation 7 may allow for the decoupling of the flash lamp from the plasma emission and background noises in an embodiment.

In step 514, signals may be collected from etch chamber with flash lamp "OFF" for the desired integration time, in step 514*a*, to measure spectrum $L_B$ in an embodiment. Spectrum $L_B$ may typically be the spectra that may be collected in the prior art that essentially has a plurality of variations associated with the measurement. The spectrum $L_B$ may be represented as follows:

$$L_B=C^{**}_{C}C^*_{FC}C_{S}I_{P} \quad \text{(equation 9)}.$$

As may be appreciated from the foregoing, coupling factors with "*" denotes quantities that may changes over time. The coupling factors with "*" being employed in equations 5-9 may represent instantaneous values from the process in real time, in an embodiment.

In step 516, a normalized optical emission spectrum $I_P$ may be calculated, in an embodiment, employing equations 10 and 11 to normalize the variations associated with the measurement system, as follows:

$$I_P=(C_{FC}/(C^*_{FC})^{1/2})((L_{GSA}/L_{GRA})(L_{AR}/L_{AS}))^{1/2}(I_G/L_{GS}) \over L_B \quad \text{(equation 10)},$$

$$I_P=((L_{GSA}/L_{GRA})(L_{AR}/L_{AS}))^{1/2}(I_G/L_{GS})L_B \quad \text{(equation 11)}.$$

As may be appreciated by the foregoing, equation 10 may be derived from equations 6, 8 and 9 with the assumptions as discussed herein. In an embodiment, the chamber may be configured to be symmetric resulting in $C_L$ to be equivalent to $C_C$. Thus, the change in $C^*_L$ may be assumed to be similar to the change in $C^*_C$ over time for a symmetric chamber.

In another embodiment, the fiber segments may be configured to be approximately equal resulting in $C_{FL}$ to be equivalent to $C_{FR}$. Thus, the change in $C^*_{FL}$ may be assumed to be similar to the change in $C^*_{FR}$ over time for equivalent fiber segments having similar exposure levels.

In yet another embodiment, the coupling factor $C_{FC}$ may be approximate to be equivalent to one for the situation wherein, for example, the collection fiber segment may be made to be very short. Furthermore, the ratio of $(C_{FC}/(C^*_{FC})^{1/2})$ may be assumed to be about one. Thus, the value $I_P$ for equation 10 may be simplified to equation 11.

In step 518, the process end point may be assessed in an embodiment. The process endpoint may be determined by the emission spectrum from $I_P$ or other methods, such as a preset time or other methods of detecting process endpoint.

If the process has not reached the endpoint, real time OES measurements may be continued to be collected in step 520 by looping back to step 510 in an embodiment. The normalized OES measurements may continue until the process has reached the endpoint. In an embodiment, loop 520 for steps 510 through 518 is the real time OES measurements.

In step 522, the process may be stopped and plasma may be turned off when the process has reached the endpoint in an embodiment.

In step 524, the processed wafer may be removed from the etch chamber in an embodiment.

In step 526, the process may continue and loop back to step 506 where a new wafer may be loaded into the etch chamber. The real time OES measurements may be collected for the processing of another wafer.

Thus, the normalization method 500 may employ OES setup as shown in FIG. 1 and off-line external calibration measurements as discussed in FIG. 2 and FIG. 3 to measure and derive normalized optical emission spectrum $I_P$ in real time. The normalized optical emission spectra are independent of the optical collection efficiencies associated with the measurement system.

As can be appreciated from the foregoing, one or more embodiments of the invention provide for a plasma processing system with the capability to facilitate quantitative comparison of optical emission spectra across multiple chambers in a manufacturing facility by employing real time OES measurements. Furthermore, the normalized spectra may be utilized to build process control and/or fault detection capabilities.

While this invention has been described in terms of several preferred embodiments, there are alterations, permutations, and equivalents, which fall within the scope of this invention. Although various examples are provided herein, it is intended that these examples be illustrative and not limiting with respect to the invention.

Also, the title and summary are provided herein for convenience and should not be used to construe the scope of the claims herein. Further, the abstract is written in a highly abbreviated form and is provided herein for convenience and thus should not be employed to construe or limit the overall invention, which is expressed in the claims. If the term "set" is employed herein, such term is intended to have its commonly understood mathematical meaning to cover zero, one, or more than one member. It should also be noted that there are many alternative ways of implementing the methods and apparatuses of the present invention. It is therefore intended that the following appended claims be interpreted as including all such alterations, permutations, and equivalents as fall within the true spirit and scope of the present invention.

What is claimed is:

1. An arrangement for in-situ optical interrogation of plasma emission to quantitatively measure normalized optical emission spectra in a plasma chamber, comprising:
   a flash lamp;
   a set of quartz windows;
   a plurality of collimated optical assemblies, said plurality of collimated optical assemblies are optically coupled to said set of quartz windows;
   a plurality of fiber optic bundles, said plurality of fiber optic bundles comprise at least an illumination fiber optic bundle, a collection fiber optic bundle, and a reference fiber optic bundle; and
   a multi-channel spectrometer, said multi-channel spectrometer is configured with at least a signal channel and a reference channel, said signal channel is optically coupled to receive light transmitted from at least said flash lamp, through at least said set of quartz windows, said set of collimated optical assemblies, said illuminated fiber optic bundle, and said collection fiber optic bundle to measure a first signal, wherein said reference channel is optically coupled to receive light from at least said flash lamp through said reference fiber optic bundle to measure a second signal simultaneously while said first signal is measured.

2. The arrangement of claim 1 wherein said flash lamp is a high-intensity, short-pulse light source.

3. The arrangement of claim 1 wherein said flash lamp is a Xenon flash lamp.

4. The arrangement of claim 1 wherein said set of quartz windows is configured with at least a first quartz window and a second quartz windows, said first quartz windows is configured diametrically opposite said second quartz window.

5. The arrangement of claim 1 wherein said first signal is an emitted signal from said plasma chamber.

6. The arrangement of claim 1, wherein said second signal is an output per pulse from said flash lamp.

7. The arrangement of claim 1 wherein said illumination fiber optic bundle is configured to have an equivalent length to said reference fiber optic bundle.

8. The arrangement of claim 1 wherein said collection fiber optic bundle and said signal channel of said multi-channel spectrometer are a matched pair, said matched pair may be performed by a first off-line calibration method.

9. A method for in-situ optical interrogation of plasma emission employing an Optical Emission Spectroscopy (EOS) arrangement to quantitatively measure normalized optical emission spectra in a plasma chamber, said method comprising:
performing a plurality of off-line calibrations;
performing a plurality of initial calibrations employing at least one of a signal channel on a multi-channel spectrometer and a reference channel on said multi-channel spectrometer;
loading an unprocessed substrate in said plasma chamber;
striking plasma to process said substrate in said plasma chamber;
performing a first set of optical interrogations for a minimum integration time with a flash lamp in an ON state while said plasma is present in said plasma chamber employing at least one of said signal channel on said multi-channel spectrometer and said reference channel on said multi-channel spectrometer;
performing a second set of optical interrogations for said minimum integration time with said flash lamp in an OFF state while said plasma is present in said plasma chamber employing at least one of said signal channel on said multi-channel spectrometer and said reference channel on said multi-channel spectrometer;
performing a third set of optical interrogations for a desired integration time with said flash lamp in said OFF state while said plasma is present in said plasma chamber employing said signal channel on said multi-channel spectrometer; and
calculating a normalized optical emission spectra.

10. The method of claim 9 wherein said EOS arrangement is configured with at least said flash lamp; a set of quartz windows; a plurality of collimated optical assemblies; a plurality of fiber optic bundles, said plurality of fiber optic bundles comprises at least an illumination fiber optic bundle, a collection fiber optic bundle, and a reference fiber optic bundle; and said multi-channel spectrometer, said multi-channel spectrometer is configured with at least said signal channel and said reference channel.

11. The method of claim 10 wherein said flash lamp is a high-intensity, short-pulse light source.

12. The method of claim 10 wherein said flash lamp is a Xenon flash lamp.

13. The method of claim 10 wherein said set of quartz windows is configured with at least a first quartz window and a second quartz windows, said first quartz windows is configured diametrically opposite said second quartz window.

14. The method of claim 10 wherein said illumination fiber optic bundle is configured to have an equivalent length to said reference fiber optic bundle.

15. The method of claim 10 wherein said collection fiber optic bundle and said signal channel of said multi-channel spectrometer are a matched pair, said matched pair may be performed by a first off-line calibration of said plurality of off-line calibrations.

16. The method of claim 9 wherein a second off-line calibration method of said plurality of off-line calibrations employs a standard light source to measure a plurality of coupling coefficients.

17. A method for in-situ optical interrogation of plasma emission employing an Optical Emission Spectroscopy (EOS) arrangement to quantitatively measure normalized optical emission spectra in a plasma chamber, said method comprising:
performing an initial calibration employing a signal channel on a multi-channel spectrometer;
loading an unprocessed substrate in said plasma chamber;
striking plasma to process said substrate in said plasma chamber;
performing a first set of optical interrogations for a minimum integration time with a flash lamp in an ON state while said plasma is present in said plasma chamber employing said signal channel on said multi-channel spectrometer;
performing a second set of optical interrogations for said minimum integration time with said flash lamp in an OFF state while said plasma is present in said plasma chamber employing said signal channel on said multi-channel spectrometer;
performing a third set of optical interrogations for a desired integration time with said flash lamp in said OFF state while said plasma is present in said plasma chamber employing said signal channel on said multi-channel spectrometer; and
calculating a normalized optical emission spectra.

18. The method of claim 17 wherein said EOS arrangement is configured with at least said flash lamp; a set of quartz windows; a plurality of collimated optical assemblies; a plurality of fiber optic bundles, said plurality of fiber optic bundles comprises at least an illumination fiber optic bundle, a collection fiber optic bundle, and a reference fiber optic bundle; and said multi-channel spectrometer, said multi-channel spectrometer is configured with at least said signal channel and said reference channel.

19. The method of claim 18 wherein said flash lamp is a high-intensity, short-pulse light source.

* * * * *